(12) United States Patent
Jansson et al.

(10) Patent No.: US 8,754,104 B2
(45) Date of Patent: *Jun. 17, 2014

(54) CRYSTALLINE SALTS OF QUINOLINE COMPOUNDS AND METHODS FOR PREPARING THEM

(71) Applicant: Active Biotech AB, Lund (SE)

(72) Inventors: Karl Jansson, Dalby (SE); Tomas Fristedt, Helsingborg (SE); Hans Wannman, Angelholm (SE); Anders Bjork, Bjarred (SE)

(73) Assignee: Active Biotech AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/669,920

(22) Filed: Nov. 6, 2012

(65) Prior Publication Data

US 2013/0123301 A1 May 16, 2013

Related U.S. Application Data

(63) Continuation of application No. 12/405,413, filed on Mar. 17, 2009, now Pat. No. 8,314,124, which is a continuation-in-part of application No. 11/050,441, filed on Feb. 4, 2005, now Pat. No. 7,589,208.

(30) Foreign Application Priority Data

Feb. 6, 2004 (SE) .................................. 0400235

(51) Int. Cl.
*A61K 31/4704* (2006.01)

(52) U.S. Cl.
USPC ......................................................... 514/312

(58) Field of Classification Search
None
See application file for complete search history.

(56) References Cited

U.S. PATENT DOCUMENTS

| | | | |
|---|---|---|---|
| 3,024,257 A | 3/1962 | Millar et al. | |
| 4,107,310 A | 8/1978 | Allais et al. | |
| 4,547,511 A | 10/1985 | Eriksoo | |
| 4,628,053 A | 12/1986 | Fries | |
| 4,738,971 A | 4/1988 | Eriksoo et al. | |
| 4,952,588 A | 8/1990 | Glamkowski et al. | |
| 5,716,638 A | 2/1998 | Touitou | |
| 5,912,349 A | 6/1999 | Sih | |
| 6,077,851 A | 6/2000 | Bjork et al. | |
| 6,121,287 A | 9/2000 | Bjork et al. | |
| 6,133,285 A | 10/2000 | Bjork et al. | |
| 6,395,750 B1 | 5/2002 | Hedlund et al. | |
| 6,593,343 B2 | 7/2003 | Bjork et al. | |
| 6,605,616 B1 | 8/2003 | Bjork et al. | |
| 6,802,422 B2 | 10/2004 | Kalvelage et al. | |
| 6,875,869 B2 | 4/2005 | Jansson | |
| 7,560,557 B2 | 7/2009 | Jansson | |
| 7,589,208 B2 * | 9/2009 | Jansson et al. ................ | 546/155 |
| 8,314,124 B2 * | 11/2012 | Jansson et al. ................ | 514/312 |
| 2002/0173520 A1 | 11/2002 | Bjork et al. | |
| 2003/0119826 A1 | 6/2003 | Manning et al. | |
| 2003/0124187 A1 | 7/2003 | Mention et al. | |
| 2005/0271717 A1 | 12/2005 | Berchielli et al. | |
| 2007/0088050 A1 | 4/2007 | Frenkel et al. | |
| 2007/0293537 A1 | 12/2007 | Patashnik et al. | |
| 2009/0162432 A1 | 6/2009 | Safadi et al. | |

FOREIGN PATENT DOCUMENTS

| | | |
|---|---|---|
| EP | 0497740 A1 | 8/1992 |
| WO | 9015052 A1 | 12/1990 |
| WO | 97/23200 A1 | 7/1997 |
| WO | 0003991 A1 | 1/2000 |
| WO | 0003992 A1 | 1/2000 |
| WO | 0130758 A1 | 5/2001 |
| WO | 03106424 A1 | 12/2003 |
| WO | 2005/041940 A1 | 5/2005 |
| WO | 2005/074899 A1 | 8/2005 |

OTHER PUBLICATIONS

Office Action issued by the US PTO dated Aug. 24, 2009 for U.S. Appl. No. 11/811,810.

* cited by examiner

*Primary Examiner* — Janet L Andres
*Assistant Examiner* — Timothy R Rozof
(74) *Attorney, Agent, or Firm* — Browdy and Neimark, PLLC

(57) ABSTRACT

A stable solid pharmaceutical composition consisting essentially of an effective amount of a crystalline salt of formula (II)

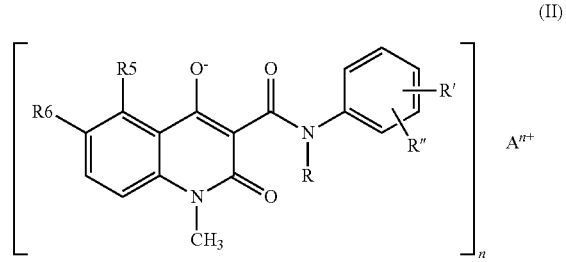

together with an alkaline-reacting component maintaining the pH preferably above 8, or a salt with a divalent metal cation; and
at least one pharmaceutical excipient;
said salt of formula (II) being essentially stable during storage at room temperature for a period of at least 3 years. A process for stabilizing the salt of formula (II).
A crystalline salt of formula (II) and a process for preparing said salt.

20 Claims, 2 Drawing Sheets

CRYSTALLINE SALTS OF QUINOLINE COMPOUNDS AND METHODS FOR PREPARING THEM

FIELD OF THE INVENTION

The present invention relates to stable compositions containing a salt of a 3-quinoline-carboxamide derivative, to methods for the manufacture of such a salt and to methods for the manufacture of a solid pharmaceutical formulation with enhanced stability during long-term storage at room temperature.

BACKGROUND OF THE INVENTION

3-Quinolinecarboxamide derivatives are described in U.S. Pat. Nos. 4,547,511, 6,077,851, 6,133,285 and 6,121,287. The term "3-quinolinecarboxamide derivative" as used in this specification designates the undissociated acid form, hereinafter called the neutral form, of the compound of formula (I), i.e., the form as given in the formula (I).

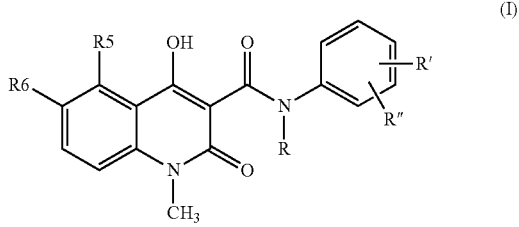

(I)

It was unexpectedly found that some 3-quinolinecarboxamide derivatives in the neutral form disclosed in the above US Patents are susceptible to chemical degradation in solid state, and, in particular, when in pharmaceutical formulations. Some salts of the 3-quinoline-carboxamide derivatives of formula (I) are known from said US Patents. However, none of the above-mentioned patent specifications discloses an enabling method of providing 3-quinoline-carboxamide derivatives of formula (I) susceptible to degradation in a sufficiently stable pharmaceutical form or even suggests any particular advantage of using the salt form of a 3-quinolinecarboxamide derivative in pharmaceutical formulations.

There are two types of solids, i.e., crystalline and amorphous. They have differences that are very important in physical pharmacy. Crystalline solids are arranged in fixed geometric patterns or lattices, and show a definite inciting point. Amorphous solids can be considered supercooled liquids in which the molecules are arranged in a random manner, somewhat as in the liquid state, and do not have definite melting points. The formation of either an amorphous or a crystalline form of a 3-quinolinecarboxamide salt wherein n is an integer of 2 or 3 is influenced by the conditions under which the salt is obtained, and the forms can be distinguished in a laboratory by X-ray powder diffraction spectroscopy.

The solid state physical property of a pharmaceutical compound is important to its dissolution, which may have stability consequences. Solid state physical properties also affect the way a pharmaceutical compound should be handled during processing into a pharmaceutical product such as a tablet or capsule formulation, e.g., physical properties can impact the type of excipients to add to a pharmaceutical formulation.

SUMMARY OF THE INVENTION

In accordance with the present invention, there is provided a stable solid pharmaceutical formulation that contains a salt of a 3-quinolinecarboxamide derivative of formula (I) with a monovalent or multivalent cation and a process for preparing said formulation. The process comprises forming a capsule or a tablet containing a salt of a 3-quinolinecarboxamide derivative and a uniformly distributed alkaline-reacting component capable of neutralising any protons dissociating from the excipients, thereby keeping the 3-quinolinecarboxamide in the salt form of formula (II).

Alternatively, the process comprises forming a capsule or a tablet containing a salt of a 3-quinolinecarboxamide derivative sparingly soluble in water and a salt with a divalent metal cation capable of lowering the dissociation of a salt of formula (II) into ions.

The alkaline-reacting component of this invention is typically sodium carbonate, and the salt with a divalent metal cation is typically calcium acetate. The solid formulation of the invention includes pharmaceutical excipients, such as solid powdered carriers, binders, disintegrants and lubricating agents.

The invention additionally provides a process for the manufacture of a crystalline salt of a 3-quinolinecarboxamide derivative of formula (I) with a counter ion that is a multivalent metal cation.

The present invention solves the problem posed by those 3-quinolinecarboxamide derivatives that are susceptible to chemical degradation in a solid pharmaceutical formulation.

DESCRIPTION OF THE INVENTION

Figure 1:
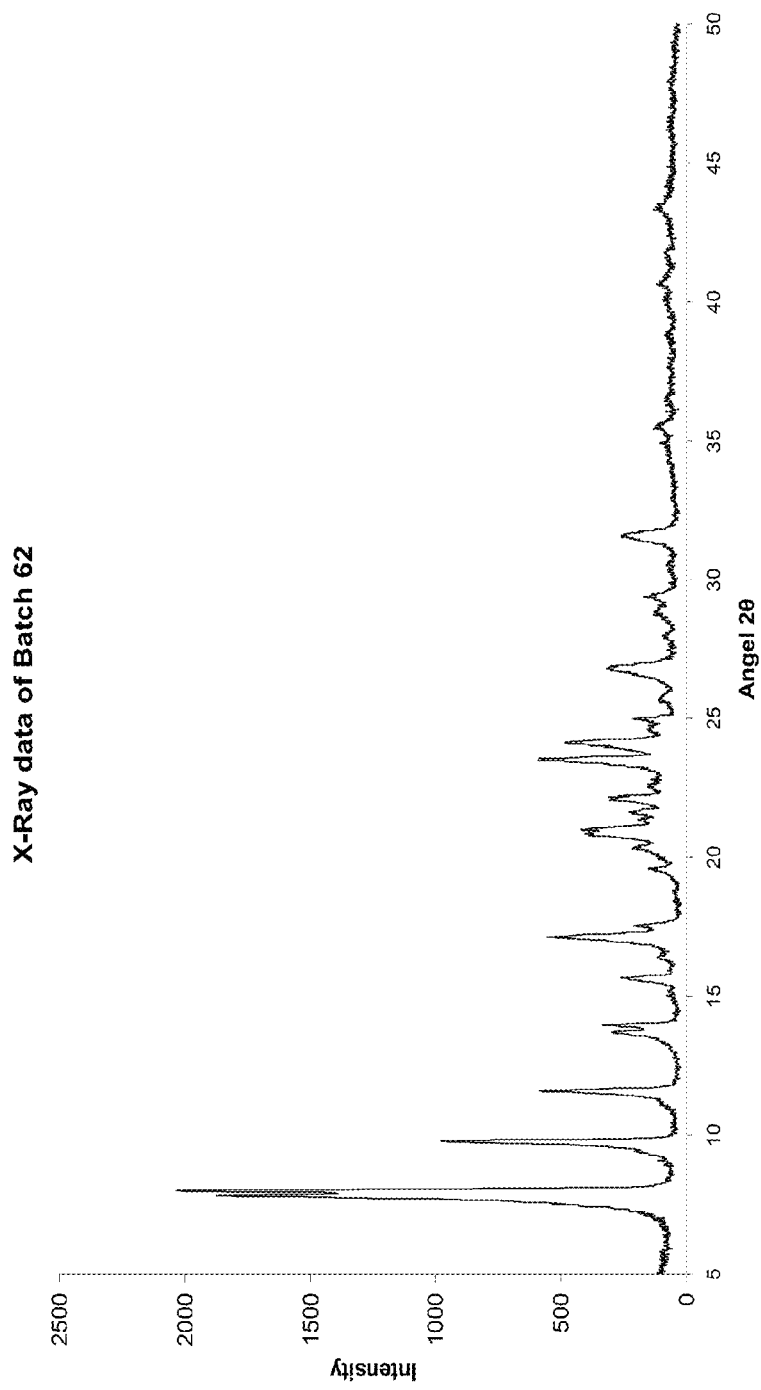
FIG. 1 shows the X-ray powder diffractogram of a crystalline salt of formula (II), prepared according to the invention.

Some 3-quinolinecarboxamide derivatives in the neutral form disclosed in the above US Patents are susceptible to chemical degradation in solid state, and, in particular, when in pharmaceutical formulations. A primary object of the present invention is to overcome this stability problem. The solution offered by the present invention to said stability problem is based on the surprising and unexpected finding that the salt form of a compound of formula (I) possesses an enhanced chemical stability compared to the neutral form of said compound.

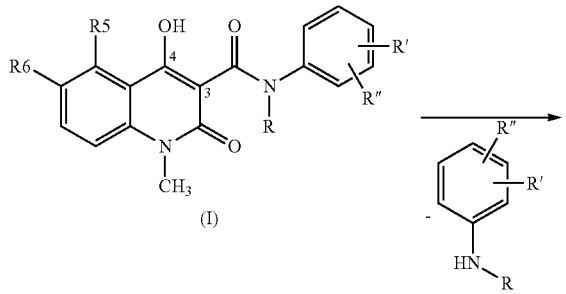

Scheme 1. The ketene formation.

(I)

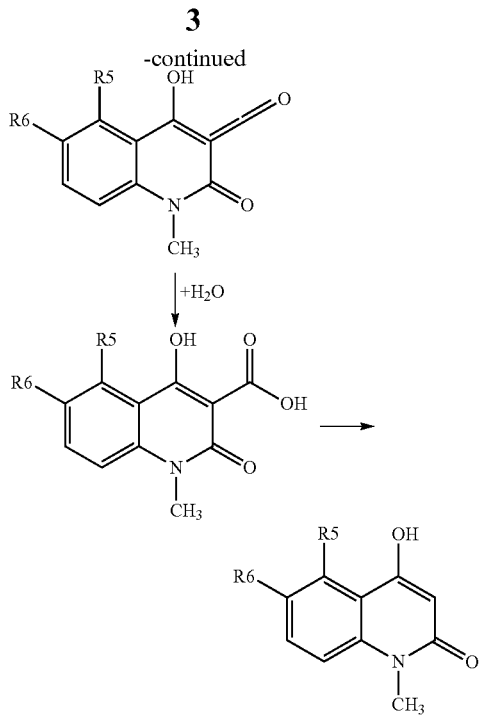

The degradation of the compounds of formula (I) was carefully investigated. The present inventors have demonstrated that the aniline moiety of the compound of formula (I) unexpectedly is eliminated and a highly reactive ketene is formed. This ketene reacts rapidly with, for example, ROH compounds.

Upon storage without any special precautions being taken, some 3-quinolinecarboxamide derivatives of formula (I) are degraded at an unacceptable rate. At storage during accelerated conditions, that is 40° C. and a relative humidity of 75%, the degradation of some 3-quinoline-carboxamide derivatives can exceed 2% in a period of 6 months (Table 1). While the rate of decomposition of 3-quinolinecarboxamide derivatives of formula CO at normal storage conditions is lower, it nevertheless is desirable to obtain a physical form of a 3-quinoline-carboxamide derivative, which exhibits improved stability.

Surprisingly and unexpectedly it has now been found that the 3-quinolinecarboxamide derivatives of formula (I), when converted to a salt form with a mono- or multivalent metal cation of the structural formula (II),

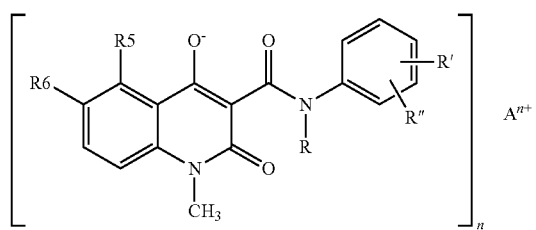

(II)

wherein n is an integer of 1, 2 or 3;

$A^{n+}$ is a mono- or multivalent metal cation selected from $Li^+$, $Na^+$, $K^+$, $Mg^{2+}$, $Ca^{2+}$, $Mn^{2+}$, $Cu^{2+}$, $Zn^{2+}$, $Al^{3+}$ and $Fe^{3+}$;

R is a straight or branched $C_1$-$C_4$-alkyl or -alkenyl or a cyclic $C_3$-$C_4$-alkyl;

R5 is a straight or branched, saturated or unsaturated $C_1$-$C_4$-alkyl or -alkenyl, a cyclic $C_3$-$C_4$-alkyl, a straight or branched $C_1$-$C_4$-alkylthio, a cyclic $C_3$-$C_4$-alkylthio, a straight or branched $C_1$-$C_4$alkylsulfinyl, a cyclic $C_3$-$C_4$-alkylsulfinyl, fluoro, chloro, bromo, trifluoromethyl or trifluoromethoxy; and R6 is hydrogen; or R5 and R6 taken together are methylenedioxy;

R' is hydrogen, a straight or branched, saturated or unsaturated $C_1$-$C_4$-alkyl or -alkenyl or a cyclic $C_3$-$C_4$-alkyl, a straight or branched $C_1$-$C_4$-alkoxy, a cyclic $C_3$-$C_4$-alkoxy, fluoro, chloro, bromo or trifluoromethyl; and R" is hydrogen, fluoro or chloro, with the proviso that R" is fluoro or chloro only when R' is fluoro or chloro;

have an enhanced stability compared to the corresponding neutral form of the 3-quinolinecarboxamides of formula (I).

A preferred group of 3-quinolinecarboxamide salts of formula (ii) are those wherein $A^{n+}$ is $Li^+$, $Na^+$ and $Ca^{2+}$.

Another preferred group of 3-quinolinecarboxamide salts of formula (II) are those salts sparingly soluble in water including $Ca^{2+}$; $Zn^{2+}$ and $Fe^{3+}$ salts.

A salt of formula (II) of a 3-quinolinecarboxamide is prepared by reacting a 3-quinoline-carboxamide of formula (I) with a mono- or multivalent metal salt. Examples of such salts and reaction conditions are given below. In general, the aqueous solubility of salts of formula (II) is higher for the salts with monovalent cations; e.g., a sodium- or potassium-salt, than for the salts with multivalent cations, e.g., a calcium, zinc, copper(II) or iron(III) salt. As an example the sodium salts are readily soluble in water but they have a limited solubility in less polar solvents, e.g., chloroform. On the contrary, an iron(III) salt is almost insoluble in water but has a high solubility in chloroform and a low solubility in methanol. When using solely aqueous solvent for the precipitation of a multivalent salt, e.g., a calcium salt of formula (II), an amorphous precipitate may form because of the very low solubility in water. However, by increasing the temperature and by adding a water miscible organic solvent, e.g., ethanol, in which the salt has somewhat higher but still a limited solubility, a crystalline compound can be precipitated. Preferably mixtures of water and ethanol, containing 10-95% ethanol are used to ensure crystalline compounds. In such mixtures the particle size of the precipitate depends on the reaction temperature, the higher temperature results in larger crystals. The reaction temperature can vary from 0° C. up to the reflux temperature. Alternatively, a crystalline salt can be prepared from an amorphous salt by mixing with a solvent in which the crystalline compound has a limited solubility as demonstrated in EXAMPLES 4 and 7.

The storage stability of a compound of formula (II) is greatly improved. This is evident from a comparison of N-ethyl-N-phenyl-5-chloro-1,2-dihydro-4-hydroxy-1-methyl-2-oxo-3-quinolinecarboxamide (hereinafter called compound A) with the sodium salt of N-ethyl-N-phenyl-5-chloro-1,2-dihydro-4-hydroxy-1-methyl-2-oxo-3-quinolinecarboxamide (hereinafter called compound A sodium). While at 40° C. and a relative humidity of 75% less than 0.01% of compound A sodium in solid state is converted to degradation products in a period of 24 months, 0.31% of compound A is degraded during a 6-month period. Another example of a 3-quinolinecarboxamide derivative susceptible to degradation is N-ethyl-N-phenyl-5-ethyl-1,2-dihydro-4-hydroxy-1-methyl-2-oxo-3-quinolinecarboxamide (hereinafter called compound B), see Table 1.

TABLE 1

Stability of 3-quinolinecarboxamide derivatives.
Storage conditions: +40° C./75% RH.

| Compound | Degradation[1] | "Shelf-life"[2] |
|---|---|---|
| A | 0.31% | >6 months |
| A sodium | <0.01%[3] | >6 months |
| B | 2.0% | <1 months |

[1]Degradation quantified as the percentage increase of related substances after 6 months of storage.
[2]"Shelf life" denotes how long the compound can be stored at the given conditions without degradation exceeding 0.5%:
[3]The same result is obtained after 24 months of storage.

Generally, any tendency of instability is exacerbated when a compound of formula (II) is formulated with various excipients. This is verified by the results from a compatibility study comparing compound A with compound A sodium shown in Table 2. It is clear that the salt form is preferred as drug substance in any binary mixtures of said compound.

TABLE 2

Compatibility studies comparing compound A with compound A sodium.
The samples are binary mixtures (1:1) of excipient and test substance.
Storage conditions: +40° C./75% RH.

| Excipient | Degradation[1] (Compound A) | Degradation[1] (Compound A sodium) |
|---|---|---|
| Microcrystalline Cellulose (Avicel PH-) | 1.1% | 0.31% |
| Maize Starch | 0.41% | 0.05% |
| Mannitol (Pearlitol 200SD) | 0.45% | 0.05% |
| Colloidal silica (Aerosil 200) | 20% | 1.5% |

[1]Degradation quantified as the percentage increase of related substances after 6 months of storage.

Said sodium salt when formulated into conventional solid pharmaceutical formulation, however, is still degraded at an unacceptable rate with a level of degradation products exceeding 5% in 6 months when stored at +40° C. and a relative humidity of 75% (Table 3). Such a level is considered problematic. An acceptable limit of degradation, under these conditions, is judged to be less than 0.5% degradation after 6 months storage. This limit is considered indicative of a 3-year shelf-life at room temperature. On the other hand, a conventional solid pharmaceutical formulation with an alkaline-reacting component also shows an unacceptable rate of degradation. The crucial step is to obtain a uniform distribution of the salt of formula (II), the alkaline-reacting component and all the pharmaceutical excipients on a molecular level.

TABLE 3

Stability data from different formulations of compound A sodium.

| Formulation | Storage | Degradation[1] | "Shelf life"[2] |
|---|---|---|---|
| Aqueous solution[3] | +2° C. to +8° C. | <0.01% | >6 months |
| Conventional tablet formulation[4] (reference) | +40° C./75% RH | 6.8% | <0.5 month |
| Conventional tablet formulation with an alkaline-reacting component[5] (reference) | +40° C./75% RH | 0.64%[7] | 1 month |
| EXAMPLE 10[6] (invention) | +40° C./75% RH | 0.16% | >6 months |

[1]Degradation quantified as the percentage increase of related substances after 6 months of storage.
[2]"Shelf life" denotes how long the formulation can be stored at the given conditions without degradation exceeding 0.5%.
[3]Composition: Compound A sodium 1 mg, sodium hydroxide 0.112 mg, water for injection ad 1 ml, pH adjusted to 7.5.
[4]Composition: Compound A sodium 0.3 mg (0.19%), microcrystalline cellulose 49.8%, lactose monohydrate 48.5%, sodium croscarmellose 0.5%, sodium stearyl fumarate 1%.
[5]Composition: Compound A sodium 0.3 mg (0.19%), pregelatinised starch 66%, mannitol 29.8%, sodium carbonate 3.0%, sodium stearyl fumarate 1.0%.
[6]Composition: According to EXAMPLE 10.
[7]Formation of related substances after 2 months of storage.

The present invention provides compositions of a salt form of a 3-quinolinecarboxamide derivative, such compositions exhibiting improved storage stability that allows the development of new pharmaceutical formulations of a 3-quinolinecarboxamide with enhanced stability during long-term, i.e., at least 3 years, storage at room temperature.

Here, the expression a "3-quinolinecarboxamide derivative susceptible to degradation" should be taken to mean a substance with a reactivity index >1.0 (see EXAMPLES, Investigation of the degradation rate below). Mechanistic studies of the ketene degradation have shown that the degradation involves an intramolecular transfer of the to enol proton in the 4-position of the quinoline ring to the nitrogen atom of the 3-carboxamide moiety (Scheme 1). It is envisaged that a stable dosage form of a compound of formula (I) would be obtained if said compound is converted to the salt form of formula (II). However, notwithstanding the enhanced chemical stability of said salt in the solid state, there still remains an unacceptable degree of instability in conventional solid dosage forms of the salts of formula (II). The reason for the instability of salts of formula (II) in conventional solid dosage forms is now believed to be linked to the exchange of the counter ion for a proton combined with the conformation of the salt in the solid state.

X-ray studies of the sodium salt of compound A demonstrated that the conformation of the solid salt is such that the exocyclic carbonyl group is bent away from the enolate oxygene atom in the 4-position. This leads to an open path between the nitrogen atom of the 3-carboxamide moiety and the enolate sodium atom in the 4-position. Without wishing to be bound to any theory of action, it is thought that this conformational property of the salts of formula (II) results in the unacceptable rate of degradation in conventional solid dosage forms once the counter ion of the salt is exchanged with a proton obtainable from the excipients.

From what is said above about the stability properties of 3-quinolinecarboxamide derivatives, it is clear that a stable dosage form of a compound of formula (I) is obtained when said compound is present and remains in the salt form of formula (II). For clinical use a salt of formula (II) of the present invention, i.e., the active ingredient, suitably is formulated into pharmaceutical solid formulations for oral mode of administration. The rigorous prevention of any conversion of said salt to the neutral form would lead to improved stability of said salts during manufacture, and during storage of the pharmaceutical formulation. Examples of such formulations are tablets and capsules. Usually the amount of active ingredient is about 0.01 to 10% by weight of the formulation, preferably about 0.1 to 2% by weight of the formulation.

Pharmaceutical compositions of the present invention contain a salt of formula (II) in combination with at least one component inhibiting degradation of the active ingredient, and pharmaceutical excipients. These compositions are one object of this invention. In one embodiment of the present invention, the composition comprises an alkaline-reacting component, which neutralises the protons. The amount of the alkaline-reacting component is dependent upon the property of said alkaline-reacting component and is about 0.1 to 99% by weight of the formulation, preferably about 1 to 20%. The pH of a specific composition is determined by adding to 2 g of the composition 4 g of de-ionised water, and then measuring the pH of the resulting slurry. The pH should preferably be above 8. Suitable alkaline-reacting components are selected from sodium, potassium, calcium and aluminium salts of acetic acid, carbonic acid, citric acid, phosphoric acid, sulphuric acid, or other suitable weak inorganic or organic acids.

In another embodiment, the composition comprises a salt with a divalent metal cation, preferably calcium acetate, and a calcium salt of formula (II). Any other salt with a divalent metal cation suitable in view of the intended application of the composition may be used, e.g., zinc and manganese salts. The amount of said salt is about 1 to 99% by weight of the formulation depending on the salt chosen. It is thought that addition of salt containing a divalent metal cation to the pharmaceutical composition would lower the dissociation of the salt of formula (II) into ions. A salt of formula (II) having a divalent metal counter ion has limited solubility. Thus the protonation of the anion of the salt of formula (II) is suppressed, which results in an increased stability. The salt of formula (II) according to the invention, is particularly advantageous when in crystalline form since the crystalline salts of formula (II) are much less prone to dissociate than a conventional salt. Hence, the use of a crystalline salt of formula (II) displaying low water-solubility and prone not to dissociate is clearly more advantageous than using the corresponding amorphous form that generally dissolves more readily.

According to one aspect, therefore, the invention provides a process for the manufacture of a crystalline salt of a 3-quinolinecarboxamide derivative of formula (I) with a counter ion that is a multivalent metal cation.

In one embodiment, the process for the preparation of a crystalline salt of formula (II)

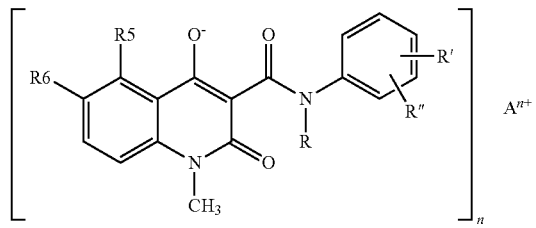

(II)

wherein
n is an integer of 2 or 3;
$An^+$ is a multivalent metal cation selected from $Mg^{2+}$, $Ca^{2+}$, $Mn^{2+}$, $Cu^{2+}$, $Zn^{2+}$, $Al^{3+}$, and $Fe^{3+}$;
R is a straight or branched C1-C4-alkyl or -alkenyl or a cyclic C3-C4-alkyl;
R5 is a straight or branched, saturated or unsaturated C1-C4-alkyl or -alkenyl, a cyclic C3-C4-alkyl, a straight or branched C1-C4-alkylthio, a cyclic C3-C4-alkylthio, a straight or branched C1-C4-alkylsulfinyl, a cyclic C3-C4-alkylsulfinyl, fluoro, chloro, bromo, trifluoromethyl or trifluoromethoxy; and
R6 is hydrogen; or
R5 and R6 taken together are methylenedioxy;
R' is hydrogen, a straight or branched, saturated or unsaturated C1-C4-alkyl or -alkenyl, cyclic C3-C4-alkyl, a straight or branched C1-C4-alkoxy, a cyclic C3-C4-alkoxy, fluoro, chloro, bromo or trifluoromethyl; and
R" is hydrogen, fluoro or chloro, with the proviso that R" is fluoro or chloro only when R' is fluoro or chloro;
includes
reacting a 3-quinolinecarboxamide derivative in neutral form or as a monovalent metal salt, e.g. a salt with an alkaline metal, such as sodium or potassium, with a salt containing the multivalent metal cation in a liquid phase consisting of water and at least one water miscible organic solvent, in which liquid phase the salt of formula (II) is sparingly soluble.

In this embodiment, it should be readily understood that the organic solvent should be selected so that the crystalline salt of formula (II), has higher solubility in the water miscible organic solvent than in water.

It is well within the capability of the skilled person to determine the solubility in water of the salt of formula (II), and to select a suitable water miscible organic solvent. For example, ethanol may be used, or any other equivalent organic solvent, e.g. methanol, 1-propanol, 2-propanol, acetonitrile, dioxan, dimethylformamide or dimethyl sulfoxide.

By "sparingly soluble", as referred to herein above, is meant a solubility higher than in water but not so high as to provide unlimited dissolution of the crystalline salt of formula (II). As a general guidance, an organic solvent wherein the crystalline salt of formula (II) has a solubility of less than 10 mg/ml, or less than 5 mg/ml, may be suitable to provide a liquid phase wherein the salt of formula (II) is sparingly soluble.

In another embodiment of the invention, the process for the preparation of a crystalline salt of formula (II)

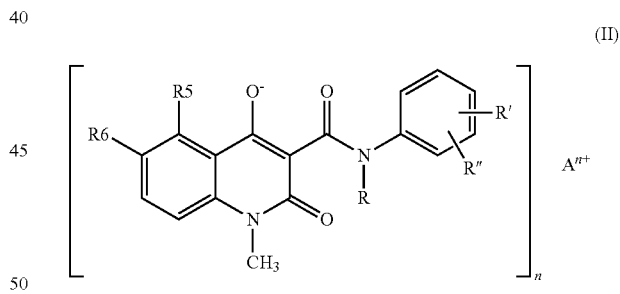

(II)

wherein
n is an integer of 2 or 3;
$An^+$ is a multivalent metal cation selected from $Mg^{2+}$, $Ca^{2+}$, $Mn^{2+}$, $Cu^{2+}$, $Zn^{2+}$, $Al^{3+}$, and $Fe^{3+}$;
R is a straight or branched C1-C4-alkyl -alkenyl or acyclic C3-C4-alkyl;
R5 is a straight or branched, saturated or unsaturated C1-C4-alkyl or -alkenyl, acyclic C3-C4-alkyl, a straight or branched C1-C4-alkylthio, acyclic C3-C4-alkylthio, a straight or branched C1-C4-alkylsulfinyl, acyclic C3-C4-alkylsulfinyl, fluoro, chloro, bromo, trifluoromethyl or trifluoromethoxy; and
R6 is hydrogen; or
R5 and R6 taken together are methylenedioxy;
R' is hydrogen, a straight or branched, saturated or unsaturated C1-C4-alkyl or -alkenyl, cyclic C3-C4-alkyl, a straight or branched C1-C4-alkoxy, a cyclic C3-C4-alkoxy, fluoro, chloro, bromo or trifluoromethyl; and R" is hydrogen, fluoro or chloro, with the proviso that R" is fluoro or chloro only when R' is fluoro or chloro;
includes
reacting a 3-quinolinecarboxamide derivative in neutral form or as a monovalent metal salt, e.g. a sodium or potassium salt, with a salt containing the multivalent metal cation in a mixture of water and a first organic solvent wherein the multivalent salt of formula (II) is soluble, so as to obtain an organic solvent solution of the multivalent salt of formula (II);

separating the first organic solvent, containing the multivalent salt of formula (II), from the aqueous phase;

precipitating the multivalent salt of formula (II) from the first organic solvent as an amorphous solid salt, preferably by evaporation;

redissolving the multivalent salt of formula (II) in a second liquid organic solvent wherein the salt has a lower solubility than in the first organic solvent; and allowing crystals of the salt of formula (II) to form in said second liquid organic solvent.

In the above method, the first organic solvent preferably is a chlorinated hydrocarbon, e.g. chloroform, while the second organic solvent preferably is selected from methanol, ethanol, n-propanol, isopropanol, acetonitrile and acetone.

According to a further aspect the invention relates to the crystalline salts of formula (II)

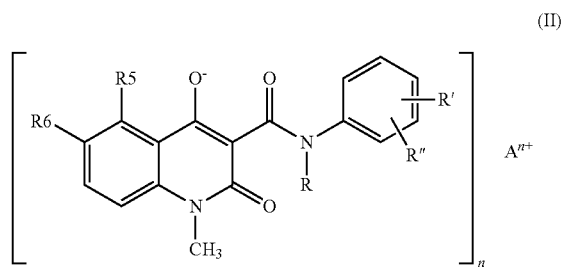

wherein
n is an integer of 2 or 3;
$A^{n+}$ is a multivalent metal cation selected from $Mg^{2+}$, $Ca^{2+}$, $Mn^{2+}$, $Cu^{2+}$, $Zn^{2+}$, $Al^{3+}$, and $Fe^{3+}$;
R is a straight or branched $C_1$-$C_4$-alkyl or -alkenyl or a cyclic $C_3$-$C_4$-alkyl;
R5 is a straight or branched, saturated or unsaturated $C_1$-$C_4$-alkyl or -alkenyl, a cyclic $C_1$-$C_4$-alkyl, a straight or branched $C_1$-$C_4$-alkylthio, acyclic $C_3$-$C_4$-alkylthio, a straight or branched $C_1$-$C_4$-alkylsulfinyl, a cyclic $C_3$-$C_4$-alkylsulfinyl, fluoro, chloro, bromo, trifluoromethyl or trifluoromethoxy; and
R6 is hydrogen; or
R5 and R6 taken together are methylenedioxy;
R' is hydrogen, a straight or branched, saturated or unsaturated $C_1$-$C_4$alkyl or -alkenyl, cyclic $C_3$-$C_4$-alkyl, a straight or branched $C_1$-$C_4$alkoxy, a cyclic $C_3$-$C_4$alkoxy, fluoro, chloro, bromo or trifluoromethyl; and
R" is hydrogen, fluoro or chloro, with the proviso that R" is fluoro or chloro only when R' is fluoro or chloro.

In one particular embodiment, the crystalline salt is a crystalline multivalent salt of N-ethyl-N-phenyl-5-chloro-1,2-dihydro-4-hydroxy-1-methyl-2-oxo-3-quinolinecarboxmide, or of N-ethyl-N-phenyl-5-ethyl-1,2-dihydro-4-hydroxy-1-methyl-2-oxo-3-quinolinecarboxamide, e.g. a crystalline divalent salt with a metal cation selected from $Ca^{2+}$ or $Zn^{2+}$.

According to another aspect, the invention relates to a stable solid pharmaceutical composition comprising a therapeutically effective amount of a crystalline salt of formula (II) as defined herein above, together with an alkaline-reacting component or a salt with a divalent metal cation; and at least one pharmaceutical excipient.

In one particular embodiment, the stable solid pharmaceutical composition comprises a crystalline multivalent salt of N-ethyl-N-phenyl-5-chloro-1,2-dihydro-4-hydroxy-1-methyl-2-oxo-3-quinolinecarboxamide, or of N-ethyl-N-phenyl-5-ethyl-1,2-dihydro-4-hydroxy-1-methyl-2-oxo-3-quinolinecarboxamide, e.g. a crystalline divalent salt with a in metal cation selected from $Ca^{2+}$ or $Zn^{2+}$.

The solid pharmaceutical composition e.g. may be in the form of a tablet or a capsule.

According to one further aspect, a method of preparing the solid pharmaceutical composition containing a therapeutically effective amount of a crystalline salt of formula (II) as defined herein above, is provided, comprising:
spraying a solution of an alkaline-reacting component onto a mixture of pharmaceutical excipients;
granulating the mixture;
drying the granulated mixture, to obtain a dry granulate;
mixing the dry granulate with a crystalline salt of formula (II), to obtain a blend of the granulate and the salt.

In one embodiment of this method, the blend of granulate and salt is compressed to obtain a tablet core and a tablet coating optionally is added to said tablet core. In another embodiment, the blend of granulate and salt is filled into a hard gelatin capsule.

According to one further aspect, a method of preparing the solid pharmaceutical composition containing a therapeutically effective amount of a crystalline salt of formula (II) as defined herein above, is provided, comprising:
mixing a crystalline salt of formula (II) and at least one pharmaceutically acceptable excipient, so as to obtain a preblend;
wet granulating the preblend with an aqueous solution of a divalent metalt salt, to obtain a granulate; and
drying the granulate.

The crystalline salt of formula (II) may be present in an amount of 0.01 to 10% by weight of the composition, e.g. 0.1 to 2% by weight of the composition.

The alkaline-reacting component of the solid pharmaceutical composition may be selected e.g. from sodium, potassium, calcium and aluminum salts of acetic acid, carbonic acid, citric acid and phosphoric acid, and may be present in an amount of 0.1 to 99% by weight of the composition, e.g. 1 to 20% by weight of the composition.

Compositions and pharmaceutical formulations containing the compounds of formula (II) described above, e.g. the crystalline salts of formula (II), are manufactured as described herein below.

In the preparation of pharmaceutical formulations in the form of dosage units for oral administration, the compound (II) is mixed with a salt with a divalent metal cation or an alkaline-reacting component and with conventional pharmaceutical excipients. Suitable excipients can be chosen among, but are not restricted to, solid powdered carriers, e.g., mannitol, microcrystalline cellulose, calcium hydrogen phosphate, calcium sulphate, and starch; binders, e.g., polyvinylpyrrolidone, starch and hydroxypropyl methylcellulose; disintegrants, e.g., sodium croscarmellose, sodium starch glycollate and polyvinylpyrrolidone as well as lubricating agents, e.g., magnesium stearate, sodium stearyl fumarate, talc and hydrogenated vegetable oil such as Sterotex NF. The mixture is then processed into tablets or granules for capsules.

According to one aspect, the present invention provides a method of preparing a tablet comprising as an active ingredient a 3-quinolinecarboxamide derivative of improved chemical stability wherein a tablet core containing a salt of formula (II) and an alkaline-reacting component, or a salt with a divalent metal cation, as well as suitable pharmaceutical excipients is manufactured. The crucial step is to achieve a tablet core with a uniform distribution, on the molecular level, of the alkaline-reacting component in order to neutralise all protons diffusing from the pharmaceutical excipients, or of the salt with a divalent metal cation in order to suppress the dissociation into ions of the salt of formula (II).

Methods of manufacturing a tablet of the invention are as follows:

a) a tablet core containing a calcium salt of formula (II) is manufactured by spraying a calcium acetate solution onto a mixture of the calcium salt of formula (II) and the pharmaceutical excipients, granulating the mixture to proper consistency, drying, and then compressing the granulate; or b) a tablet core containing a salt of formula (II) sparingly soluble in water is manufactured by spraying a solution of an alkaline-reacting component onto a mixture of the pharmaceutical excipients, granulating the mixture to proper consistency, drying, mixing with a crystalline salt of formula (II) sparingly soluble in water, and then compressing the final blend; or c) a tablet core containing a lithium, sodium or potassium salt of formula (II) is manufactured by spraying a solution of the salt of formula (II) and an alkaline-reacting component onto a mixture of the pharmaceutical excipients, granulating the mixture to proper consistency, drying, and then compressing the granulate; and d) a lubricating agent may optionally be added to the granulate prior to compression; and e) a coating layer is optionally added to said core using conventional coating pharmaceutical excipients.

A preferred method of manufacturing a tablet of the invention is:

f) a tablet core containing a sodium salt of formula (II) is manufactured by spraying a solution of a sodium salt of formula (II) and an alkaline-reacting component onto a mixture of the pharmaceutical excipients, granulating the mixture to proper consistency, drying, and then compressing the granulate. A lubricating agent may optionally be added to the granulate prior to compression, and a coating layer is optionally added to said core using conventional coating pharmaceutical excipients.

According to another aspect, the present invention provides a method of preparing a capsule comprising as an active ingredient a 3-quinolinecarboxamide derivative of improved chemical stability.

Methods of manufacturing a capsule of the invention are as follows:

g) a mixture containing a calcium salt of formula (II) is manufactured by spraying a calcium acetate solution onto a mixture of the calcium salt of formula (II) and the pharmaceutical excipients, granulating the mixture to proper consistency, and subsequently drying the granulate; or h) a mixture containing a salt of formula (II) sparingly soluble in water is manufactured by spraying a solution of an alkaline-reacting component onto a mixture of the pharmaceutical excipients, granulating the mixture to proper consistency, drying the granulate, and mixing with a crystalline salt of formula (II) sparingly soluble in water; or i) a mixture containing a lithium, sodium or potassium salt of formula (II), more preferably a sodium salt, is manufactured by spraying a solution of the salt of formula (II) and an alkaline-reacting component onto a mixture of the pharmaceutical excipients, granulating the mixture to proper consistency, and subsequently drying the granulate;

j) a lubricating agent is optionally added to the mixture; and k) the final blend is filled into hard gelatine capsules.

An alternative method of preparing a salt of formula (II), which then has to be readily soluble in water, is to dissolve the corresponding compound of formula (I) in the neutral form in a solution of an alkaline reacting component such as sodium carbonate, thus producing the salt of formula (II) in-situ, and subsequently follow the methods as described above.

EXAMPLES

The examples below are given with the intention to illustrate the invention without limiting the scope thereof.

Example 1

Investigation of the Degradation Rate

The degradation rate, hereinafter called the reactivity index, of compound of formula (I) was determined in solution. Roquinimex (Merck Index 12th Ed., No. 8418; Linomide®, LS2616, N-methyl-N-phenyl-1,2-dihydro-4-hydroxy-1-methyl-2-oxo-3-quinolinecarboxamide) was selected as a reference compound with the reactivity index defined to 1.0. A medium of 1-% 0.01M hydrochloric acid in n-propanol was selected. The reaction temperature was in the range of 45 to 60° C. The 3-quinolinecarboxamide derivative of formula (I) was added to the n-propanol solution. The reaction transfers the compound to an n-propylester. The reaction was stopped after 0, 2 and 4 hours, and analysis was carried out by means of HPLC with UV detection. The disappearance of the 3-quinolinecarboxamide derivative was used for evaluation of the reactivity index, but as an alternative also the formation of the n-propylester may be used. A reactivity index of corresponds to a degradation rate of 13% per hour at 60° C., a reactivity index of 2.0 corresponds to a degradation rate of 26% per hour etc. The reactivity indices of some compounds of formula (I) are shown in Table 4.

TABLE 4

Reactivity index of compounds of formula (I).

| | Structure in relation to compound (I) | | | Reactivity |
| --- | --- | --- | --- | --- |
| Compound | R5, R6 | R', R'' | R | index |
| Roquinimex | H | | H | methyl | 1.0 (defined) |
| A | 5-chloro | H | ethyl | 3.1 |
| B | 5-ethyl | H | ethyl | 4.6 |
| C | 5-chloro | 2,4-F$_2$ | methyl | 2.6 |
| D | 5-methyl | 4-CF$_3$ | methyl | >10 |
| E | 5,6-methylenedioxy | H | ethyl | 2.9 |
| F | 5-methylthio | H | ethyl | >10 |

Compound A is N-ethyl-N-phenyl-5-chloro-1,2-dihydro-4-hydroxy-1-methyl-2-oxo-3-quinolinecarboxamide;

Compound B is N-ethyl-N-phenyl-5-ethyl-1,2-dihydro-4-hydroxy-1-oxo-3-quinolinecarboxamide;

Compound C is N-methyl-N-(2,4-difluorophenyl)-5-chloro-1,2-dihydro-4-hydroxy-1-methyl-2-oxo-3-quinolinecarboxamide;

Compound D is N-methyl-N-(4-trifluorophenyl)-1,2-dihydro-1,5-dimethyl-4-hydroxy-1-methyl-2-oxo-3-quinolinecarboxamide;

Compound E is N-ethyl-N-phenyl-5,6-methylenedioxy-1,2-dihydro-4-hydroxy-1-methyl-2-oxo-3-quinolinecarboxamide; and Compound F is N-ethyl-N-phenyl-5-methylthio-1,2-dihydro-4-hydroxy-1-methyl-2-oxo-3-quinolinecarboxamide.

The following detailed Examples 2 to 7 serve to illustrate the process for manufacturing to the compounds of formula (II), which are used in the pharmaceutical formulations according to the present invention.

Example 2

N-Ethyl-N-phenyl-5-chloro-1,2-dihydro-4-hydroxy-1-methyl-2-oxo-3-quinolinecarboxamide sodium salt N-Ethyl-N-phenyl-5-chloro-1,2-dihydro-4-hydroxy-1-methyl-2-oxo-3-quinolinecarboxamide (28 mmol, 10.0 g) was suspended in 99.5% ethanol (150 ml) and 5 M aqueous sodium hydroxide solution (28.4 mmol, 5.68 ml) was added. The reaction mixture was stirred for 30 minutes at ambient temperature. The resulting crystalline precipitate was isolated by filtration, rapidly washed twice with cold ethanol (2×150 ml), and dried in vacuum over $P_2O_5$ to give the title compound (9.5 g, 90% yield), Anal, Calcd for $C_{19}H_{16}ClN_2O_3Na$: C, 60.2; H, 4.26; N, 7.40. Found C, 60.4; H, 4.20; N, 7.32. The solubility in water at room temperature was 138 mg/ml.

Example 3

N-Ethyl-N-phenyl-5-chloro-1,2-dihydro-4-hydroxy-1-methyl-2-oxo-3-quinolinecarboxamide calcium salt N-Ethyl-N-phenyl-5-chloro-1,2-dihydro-4-hydroxy-1-methyl-2-oxo-3-quinolinecarboxamide sodium salt (2.63 mmol, 1.0 g) was dissolved in a mixture of ethanol (10.5 ml) and water (5.3 ml). The solution was heated to 70° C. and a solution of calcium acetate hydrate in water (1M solution, 1.05 eq., 1.38 mmol, 1.38 ml) was added. The resulting suspension was stirred for 30 minutes, then cooled, and the crystals were isolated by filtration, washed with water, and dried under vacuum (966 mg, 98% yield). Anal. Calcd for $C_{38}H_{32}Cl_2N_4O_6Ca$: C, 60.7; H, 4.29; N, 7.45. Found C, 60.5; H, 4.34; N, 7.41.

The solubility in water at room temperature was about 1.0 mg/ml. The salt is considered as sparingly soluble in water.

Example 4

N-Ethyl-N-phenyl-5-chloro-1,2-dihydro-4-hydroxy-1-methyl-2-oxo-3-quinolinecarboxamide iron (III) salt N-Ethyl-N-phenyl-5-chloro-1,2-dihydro-4-hydroxy-1-methyl-2-oxo-3-quinolinecarboxamide sodium salt (5.0 g, 13.2 mmol) was dissolved in water (80 ml) at 40° C. and chloroform (100 ml) was added. A solution of iron(III)sulphate pentahydrate (0.95 eq., 2.09 mmol, 1.023 g) dissolved in water (30 ml) was added. The two-phase system was stirred vigorously and pH in the aqueous phase was adjusted to 8 with 1 M NaOH. The deep-red organic phase was separated, dried with sodium sulphate, and solvents were removed to give the title compound as a red amorphous glassy mass (4.22 g, 85% yield). MS-ESI: m/z 1122 [MH]+. The glassy mass was dissolved in methanol and red crystals of the title compound were formed. The crystals were filtered, washed with methanol, and dried under vacuum to give the title compound (3.96 g, 80% yield). Anal. Calcd for $C_{57}H_{48}N_6O_9Cl_3Fe$: C, 61.0; H, 4.31; N, 7.48, Found C, 62.7; H, 4.37; N, 7.27, EDTA-titriometric determination of iron (III) gave a content of 4.90% (theoretical content is 4.97%).

Example 5

N-Ethyl-N-phenyl-5-ethyl-1,2-dihydro-4-hydroxy-1-methyl-2-oxo-3-quinolinecarboxamide lithium salt N-Ethyl-N-phenyl-5-ethyl-1,2-dihydro-4-hydroxy-1-methyl-2-oxo-3-quinolinecarboxamide (4.39 mmol, 1.539 g) was suspended in ethanol (7.5 ml) and a solution of lithium hydroxide hydrate (1.05 eq. 4.61 mind, 195 mg) dissolved in water (1.5 ml) was added. The mixture was stirred for 4 h and ethyl acetate (30 ml) was added. After stirring for 1 h the crystals were filtered, washed with ethyl acetate, and dried under vacuum to furnish the title product (1.31 g, 84% yield). Anal. Calcd for $C_{21}H_{21}N_2O_3Li$: C, 70.8; H, 5.94; N, 7.86. Found C, 70.5; H, 5.22; N, 8.01.

The solubility in water at room temperature was 18 mg/ml.

A divalent crystalline salt of formula (II) was prepared by a method of the invention, as described in EXAMPLE 6A.

Example 6A

Crystalline N-Ethyl-N-phenyl-5-ethyl-1,2-dihydro-4-hydroxy-2-methyl-2-oxo-3-quinolinecarboxainide calcium salt N-Ethyl-N-phenyl-5-ethyl-1,2-dihydro-4-hydroxy-1-methyl-2-oxo-3-quinolinecarboxamide (5.0 g, 14.2 mmol) was dissolved in a mixture of 1M NaOH (14.26 mmol, 14.26 ml) and ethanol (30 ml), and pH was adjusted to 7.5. The solution was heated to 70° C. and calcium acetate hydrate (1.05 eq., 7.5 mmol, 1.335 g) in water (7 ml) was added dropwise during 5 min. The heating was discontinued and the mixture was stirred at room temperature for 1 h, the crystals were filtered, washed with ethanol/water 1/1, and dried under vacuum to afford the title compound (5.16 g, 98% yield). Anal. Calcd for $C_{42}H_{42}N_4O_6Ca$: C, 68.3; H, 5.73; N, 7.58. Found C, 68.4; H, 5.72; N, 7.63. EDTA-titriometric determination of calcium gave a content of 5.42% (theoretical content is 5.42%).

The solubility in water at room temperature was 0.3 mg/ml.

The crystalline state of the product salt obtained by the inventive method was confirmed by X-ray powder diffraction analysis (FIG. 1).

The calcium salt of N-Ethyl-N-phenyl-5-ethyl-1,2-dihydro-4-hydroxy-1-methyl-2-oxo-3-quinolinecarboxamide was also prepared by a conventional method according to the prior art, as described in EXAMPLE 6B.

Example 6B

Amorphous N-ethyl-N-phenyl-5-ethyl-1,2-dihydro-4-hydroxy-1-methyl-2-oxo-3-quinolinecarboxamide calcium salt (batch 56)

N-ethyl-N-phenyl-5-ethyl-1,2-dihydro-4-hydroxy-1-methyl-2-oxo-3-quinolinecarboxamide (28.5 mmol, 10.0 g) was dissolved in a mixture of water (200 mL) and 10M NaOH (28.5 mmol, 2.85 mL), and pH was adjusted to 7.5-8.0 with 1M HCl. To this solution at 50° C. was added during 15 min a solution of calcium acetate hydrate (15 mmol, 2.67 g) in water (50 ml) and the resultant thick emulsion was allowed to cool to room temperature and the precipitate was filtered and washed with water. The precipitate was dried in vacuum to give 8.96 g of an amorphous calcium salt.

Figure 2:
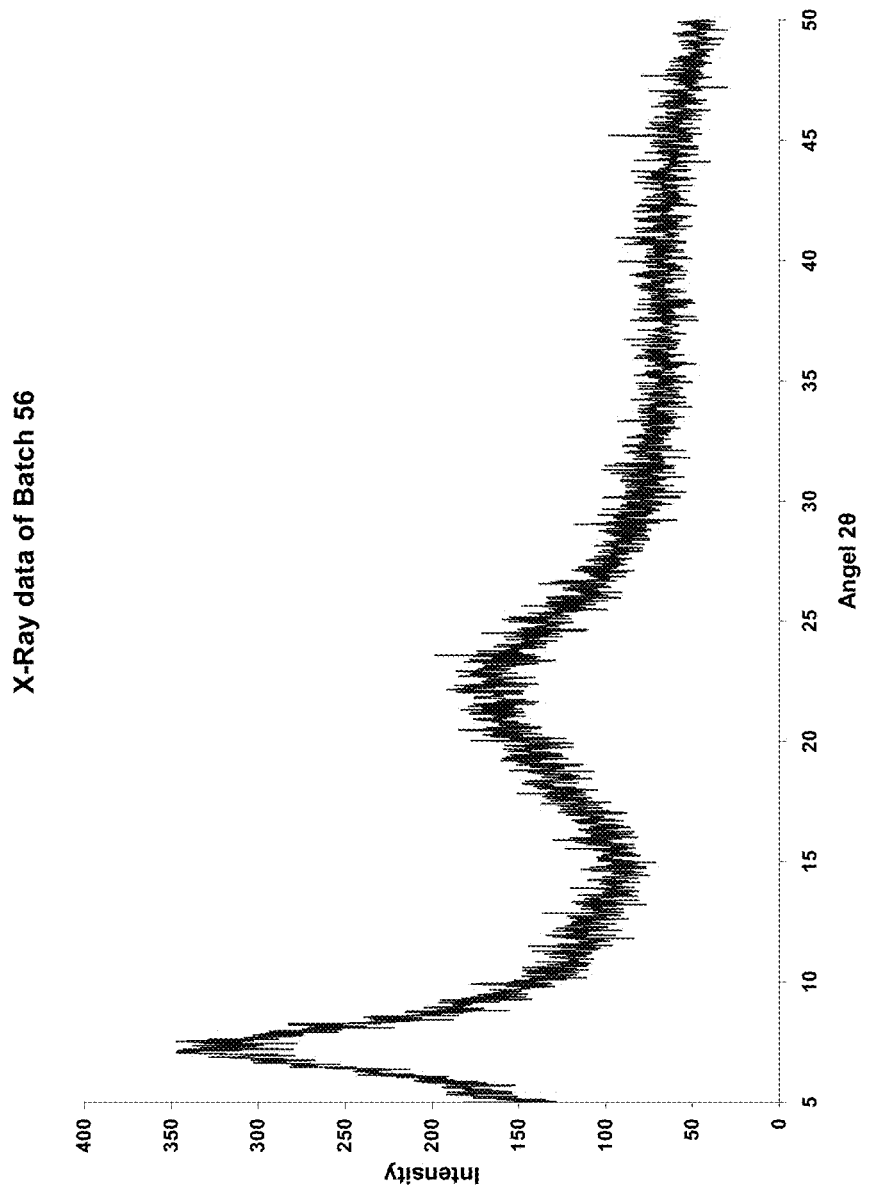
FIG. 2 shows the X-ray powder diffractogram of an amorphous salt of formula (II), prepared according to the prior art.

The amorphous state of the product salt obtained by the convention method was confirmed by X-ray powder diffraction analysis (FIG. 2).

Example 7

N-Ethyl-N-phenyl-5-ethyl-1,2-dihydro-4-hydroxy-1-methyl-2-oxo-3-quinolinecarboxamide zinc salt N-Ethyl-N-phenyl-5-ethyl-1,2-dihydro-4-hydroxy-1-methyl-2-oxo-3-quinolinecarboxamide (1.0 g, 2.85 mmol) was dissolved in a mixture of 1M NaOH (2.95 mmol, 2.95 ml) and ethanol (6.0 ml). Chloroform (20 ml) and water (40 ml) were added followed by addition of zinc acetate dihydrate (3.0 mmol, 660 mg). The two-phase mixture was stirred vigorously for 10 min, the organic phase was separated and dried with sodium sulphate and the solvents were removed. The residue was recrystallised from methanol to give the title compound (823 mg, 76% yield). Anal. Calcd for $C_{42}H_{42}N_4O_6Zn$: C, 66.01; H, 5.54; N, 7.33. Found C, 65.4; H, 5.68; N, 7.29. EDTA-titriometric determination of zinc gave a content of 8.45% (theoretical content is 8.50%), The solubility in water at room temperature was 0.3 mg/ml.

Example 8

Description of Manufacturing

A pharmaceutical formulation according to the present invention, in the form of capsules, having the following composition was prepared:

| | Granulate 0.17% | |
|---|---|---|
| Solid excipients | Mannitol | 96.8% |
| | Sodium carbonate | 3.00% |
| Granulation fluid | Compound A sodium[1] | 0.18% |
| | Sodium carbonate | 0.03% |
| | Water (13.3% of solid excipients) | na[2] |
| | Capsules | |
| Final blend | Compound A sodium Granulate 0.17% | 99.0% |
| | Sodium stearyl fumarate | 1.00% |

[1]The compound given above may be replaced with another compound of the present invention.
[2]The water is removed during drying.

Compound A sodium was dissolved in aqueous sodium carbonate and wet granulated together with mannitol and additional sodium carbonate. All excipients required for capsule filling except, the lubricant were present in the granulation step. The resulting granulate was dried in a conventional manner and passed through a screen of suitable size. The dry granules were mixed well with sodium stearyl fumarate and the mixture obtained was filled into capsules. The capsules contained suitable amounts of the active ingredient.

Example 9

Description of Manufacturing

A pharmaceutical formulation according to the present invention, in the form of capsules, having the following composition was prepared:

| | Granulate 0.18% | |
|---|---|---|
| Solid excipients | Compound B calcium[1] | 0.19% |
| | Mannitol | 65.0% |
| | Microcrystalline cellulose | 32.0% |
| Granulation fluid | Calcium acetate | 3.00% |
| | Water (50.0% of solid excipients) | na[2] |

[1]The compound given above may be replaced with another compound of the present invention.
[2]The water is removed during drying.

A preblend of compound B calcium, mannitol and microcrystalline cellulose was prepared. The preblend was wet granulated with an aqueous calcium acetate solution. All excipients required for capsule filling were present in the granulation step. The resulting granulate was dried in a conventional manner and passed through a screen of suitable size. The dry granules were filled into capsules. The capsules contained suitable amounts of the active ingredient.

Example 10

Description of Manufacturing

A pharmaceutical formulation according to the present invention, in the form of tablets, having the following composition was prepared:

| | Granulate 0.19% | |
|---|---|---|
| Solid excipients | Mannitol | 30.0% |
| | Pregelatinised starch | 66.8% |
| | Sodium carbonate | 2.84% |
| Granulation fluid | Compound A sodium[1] | 0.20% |
| | Sodium carbonate | 0.20% |
| | Water (35.8% of solid excipients) | na[2] |
| | Tablets | |
| | Compound A sodium Granulate 0.19% | 93.1% |
| | Sodium stearyl fumarate | 0.94% |
| | Coating suspension | |
| | Opadry 03B28796 White | 6.00% |

[1]The compound given above may be replaced with another compound of the present invention.
[2]The water is removed during drying.

Compound A sodium was dissolved in aqueous sodium carbonate and wet granulated together with mannitol, pregelatinised starch and additional sodium carbonate. All excipients required for tabletting except the lubricant were present in the granulation step. The resulting granulate was dried in a conventional manner and passed through a screen of suitable size. The dry granules were mixed well with sodium stearyl fumarate and the mixture obtained was compressed to tablets. The tablets were coated with a film on Opadry 03B28796 White. The tablets contained suitable amounts of the active ingredient.

Example 11

Description of Manufacturing

A pharmaceutical formulation according to the present invention, in the form of tablets, having the following composition was prepared:

| Granulate 0.18% | | |
|---|---|---|
| Solid excipients | Mannitol | 32.0% |
| | Microcrystalline cellulose | 65.8% |
| Granulation fluid | Compound A sodium[1] | 0.20% |
| | Sodium carbonate | 0.20% |
| | Sodium hydrogen carbonate | 1.80% |
| | Water (50.0% of solid excipients) | na[2] |
| Tablets | | |
| | Compound A sodium Granulate 0.18% | 99.0% |
| | Sodium stearyl fumarate | 1.00% |

[1]The compound given above may be replaced with another compound of the present invention.
[2]The water is removed during drying.

Compound A sodium was dissolved in aqueous solution of a sodium carbonate/sodium hydrogen carbonate mixture and wet granulated together with mannitol and microcrystalline cellulose. All excipients required for tabletting except the lubricant were present in the granulation step. The resulting granulate was dried in a conventional manner to and passed through a screen of suitable size. The dry granules were mixed well with sodium stearyl fumarate and the mixture obtained was compressed to tablets. The tablets contained suitable amounts of the active ingredient.

Example 12

Description of Manufacturing

A pharmaceutical formulation according to the present invention, in the form of tablets, having the following composition was prepared:

| Granulate 0.18% | | |
|---|---|---|
| Solid excipients | Mannitol | 48.5% |
| | Calcium sulphate dihydrate | 48.3% |
| | Sodium carbonate | 3.02% |
| Granulation fluid | Compound A sodium[1] | 0.19% |
| | Sodium carbonate | 0.01% |
| | Water (6.7% of solid excipients) | na[2] |
| Tablets | | |
| | Compound A sodium Granulate 0.18% | 99.0% |
| | Sodium stearyl fumarate | 1.00% |

[1]The compound given above may be replaced with another compound of the present invention.
[2]The water is removed during drying.

Compound A sodium was dissolved in aqueous sodium carbonate solution and wet granulated together with mannitol, calcium sulphate dihydrate and additional sodium carbonate. All excipients required for tabletting except the lubricant were present in the granulation step and the resulting granule was dried in a conventional manner. The dry granules were mixed well with sodium stearyl fumarate and the mixture obtained was to compressed to tablets. The tablets contained suitable amounts of the active ingredient.

We claim:

1. A stable solid pharmaceutical composition comprising a salt of N-ethyl-N-phenyl-1,2-dihydro-4-hydroxy-5-chloro-1-methyl-2-oxoquinoline-3-carboxamide, at least one pharmaceutical excipient, and a component which neutralizes protons diffusing from the at least one pharmaceutical excipient.

2. The stable solid pharmaceutical composition of claim 1, wherein the component which neutralizes protons diffusing from the at least one pharmaceutical excipient is an alkaline-reacting-component.

3. The stable solid pharmaceutical composition of claim 1, wherein the component which to neutralizes protons diffusing from the at least one pharmaceutical excipient is uniformly distributed in the composition.

4. The stable solid pharmaceutical composition of claim 2, wherein the alkaline-reacting-component is uniformly distributed in the composition.

5. The stable solid pharmaceutical composition of claim 1, wherein the salt of N-ethyl-N-phenyl-1,2,-dihydro-4-hydroxy-5-chloro-1-methyl-2-oxoquinoline-3-carboxamide is a sodium salt.

6. The stable solid pharmaceutical composition of claim 2, wherein the salt of N-ethyl-N-phenyl-1,2,-dihydro-4-hydroxy-5-chloro-1-methyl-2-oxoquinoline-3-carboxamide is a sodium salt.

7. The stable solid pharmaceutical composition of claim 3, wherein the salt of N-ethyl-N-phenyl-1,2,-dihydro-4-hydroxy-5-chloro-1-methyl-2-oxoquinoline-3-carboxamide is a sodium salt.

8. The stable solid pharmaceutical composition of claim 4, wherein the salt of N-ethyl-N-phenyl-1,2,-dihydro-4-hydroxy-5-chloro-1-methyl-2-oxoquinoline-3-carboxamide is a sodium salt.

9. The stable solid pharmaceutical composition of claim 5, comprising one or more of a solid powdered carrier, binder, disintegrant and lubricating agent, wherein the solid powdered carrier is selected from the group consisting of mannitol microcrystalline cellulose, calcium hydrogen phosphate, calcium sulphate and starch, wherein the binder is selected from the group consisting of polyvinylpyrrolidone, starch and hydroxypropyl methylcellulose, wherein the disintegrant is selected from the group consisting of sodium croscarmellose, sodium starch glycoliate and polyvinylpyrrolidone, and wherein the lubricating agent is selected from the group consisting of magnesium stearate, sodium stearyl to fumarate, talc and hydrogenated vegetable oil.

10. The stable solid pharmaceutical composition of claim 5, which comprises magnesium stearate.

11. The stable solid pharmaceutical composition of claim 5, which comprises mannitol and magnesium stearate.

12. The stable solid pharmaceutical composition of claim 5, which comprises mannitol and sodium stearyl fumarate.

13. The stable solid pharmaceutical composition of claim 6, which comprises mannitol and sodium stearyl fumarate.

14. The stable solid pharmaceutical composition of claim 7, which comprises mannitol and sodium stearyl fumarate.

15. The stable solid pharmaceutical composition of claim 8, which comprises mannitol and sodium stearyl fumarate.

16. The stable solid pharmaceutical composition of claim 1, wherein the salt of N-ethyl-N-phenyl-1,2,-dihydro-4-hydroxy-5-chloro-1-methyl-2-oxoquinoline-3-carboxamide is present in an amount of 0.1-2% by weight of the composition.

17. The stable solid pharmaceutical composition of claim 10, wherein the salt of N-ethyl-N-phenyl-1,2,-dihydro-4-hydroxy-5-chloro-1-methyl-2-oxoquinoline-3-carboxamide is present in an amount of 0.1-2% by weight of the composition.

18. The stable solid pharmaceutical composition of claim 11, wherein the salt of N-ethyl-N-phenyl-1,2,-dihydro-4-hydroxy-5-chloro-1-methyl-2-oxoquinoline-3-carboxamide is present in an amount of 0.1-2% by weight of the composition.

19. The stable solid pharmaceutical composition of claim 5 in the form of a capsule or a tablet.

20. The stable solid pharmaceutical composition of claim 16 in the form of a capsule or a tablet.

* * * * *